United States Patent [19]

White

[11] 4,129,417

[45] Dec. 12, 1978

[54] MULTISYSTEM TEST MEANS

[75] Inventor: William I. White, Elkhart, Ind.

[73] Assignee: Miles Laboratories, Inc., Elkhart, Ind.

[21] Appl. No.: 846,441

[22] Filed: Oct. 28, 1977

[51] Int. Cl.² ............................................. G01N 33/16
[52] U.S. Cl. ............................ 23/230 B; 195/103.5 R; 252/408; 422/58
[58] Field of Search ....................... 23/253 TP, 230 B; 195/103.5 R; 252/408

[56] References Cited

U.S. PATENT DOCUMENTS

| | | | |
|---|---|---|---|
| 3,006,735 | 10/1961 | Jordan | 23/253 TP |
| 3,008,879 | 11/1961 | Harvill | 23/253 TP |
| 3,645,853 | 2/1972 | Kronish et al. | 195/103.5 R |
| 3,960,489 | 6/1976 | Giaever | 23/230 B |
| 3,964,871 | 6/1976 | Hochstrasser | 23/253 TP |
| 3,979,509 | 9/1976 | Giaever | 23/253 TP |
| 4,011,308 | 3/1977 | Giaever | 23/253 TP |

*Primary Examiner*—R.E. Serwin
*Attorney, Agent, or Firm*—Charles J. Herron

[57] ABSTRACT

Multisystem test means, method of making same and method for determining a constituent in a sample under a plurality of reaction parameters. More particularly, a multisystem test means for the determination of a constituent in a liquid sample comprising a plurality of components associated with at least two reaction systems, said reaction system being respectively functional under different reaction parameters, at least one of said components being responsive to the presence of said constituent, and at least one other of said components being effective in response to contact with the sample under reaction parameters at which a first of said reaction systems is functional to change said reaction parameters to those under which at least one other of said reaction systems is functional. The test means, or device incorporated therewith, is contacted with a sample to be tested and after a predetermined time at least one component causes a change in reaction parameters.

34 Claims, No Drawings

4,129,417

MULTISYSTEM TEST MEANS

BACKGROUND OF THE INVENTION

The present invention relates generally to the field of reagent tests and, more particularly, to a multisystem test means and method for detecting a constituent in reaction systems functional under different reaction parameters.

The prior art has developed a wide variety of test means for the determination of specific constituents in liquids such as urine and blood. These have taken a variety of forms, one of the most popular being reagent impregnated test strips of the dip-and-read type, certain of which are useful for the determination of such constituents as glucose, protein, occult blood, and the like in body fluids, whereas others are useful for the determination of various constituents in other liquids, such as swimming pool water, cutting fluids, and the like.

Such prior art test systems have conventionally been of the single phase type which include in the reagent composition one or more components, for example a buffer, for maintaining the environmental parameters for the test reaction within a specific range, such as a single specific pH range, which is necessary for the desired reaction to take place.

Such test systems have included those which comprise more than one reaction and, to the extent that such reactions are operable under the same reaction conditions, such systems have been satisfactory. However, there are a number of situations involving more than one reaction wherein the respective reactions necessarily or optimally function only under different reaction conditions, for example different pH levels. The use in such a system of means for maintaining a single reaction condition or environment, for example a pH within a specific limited range, results in one or more of the system reactions being carried out under less than optimum conditions.

Prior art systems wherein a plurality of reactions are carried out under a single set of reaction parameters have the further drawback that certain reaction component candidates which exhibit superior performance characteristics cannot be used therein because they are inoperable as a component of one reaction under reaction conditions required by another reaction of the system.

While these prior art single phase systems have filled a great need, the chemical methodologies to which they are applicable have been limited in scope. Substantial areas of analysis have not heretofore been possible with conventional test systems because of the limitations inherent in the maintenance therein of reaction parameters within a single relatively narrow range. The areas of analysis to which the prior art test systems are not applicable comprise a wide variety of analytical methods which include multiple reactions which optimally or necessarily function under different reaction or environmental parameters, for example different pH, ionic strength, reactants present, and others. Such can include the presence of interfering substances which must be inactivated to allow for reliable constituent determinations and delayed addition of components which are either labile or deleterious under certain conditions.

OBJECTS OF THE INVENTION

It is a principal object of the present invention to provide a multisystem test means for the determination of a constituent in a sample which upon contact with the test sample under reaction parameters conducive to response of at least one reaction system produces different reaction parameters conducive to the functioning of at least one other reaction system.

It is another object to provide a multisystem test means having at least one component responsive to the constituent to be determined and at least one other component functional to change reaction parameters.

It is yet another object to provide a process for preparing the abovementioned multisystem test means.

An additional object of the invention is to provide multisystem test means for undertaking analytical methods requiring intermediate variation of reaction parameters by a single operation.

A further object is to provide a rapid and convenient method for determining a constituent in a sample using the abovementioned multisystem test means.

Another object of the invention is to provide the abovementioned multisystem test means in the format of an unitary device.

Other objects and a fuller understanding of the invention will be had by referring to the following description and claims drawn to preferred embodiments thereof.

SUMMARY OF THE INVENTION

In accordance with the present invention there is provided a novel multisystem test means, method of making same and method for determining a constituent in a liquid sample under a plurality of reaction parameters by the multisystem test means. More particularly, there is provided a multisystem test means for the determination of a constituent in a sample comprising a plurality of components associated with at least two reaction systems, said reaction systems being respectively functional under different reaction parameters, at least one of said components being responsive to the presence of said constituent and at least one other of said components being effective in response to contact with the sample under reaction parameters at which a first of said reaction systems is functional to change said reaction parameters to those under which at least one other of said reaction systems is functional. The test means can comprise more than one constituent responsive component. The constituent responsive component can advantageously be a chromophoric indicator, an antigen, antibody, enzyme or other specific binding partner or the like. Among the parameters which the device can be designed for changing, modification of pH, ionic strength, reagents present, such as interfering substances, and rate of reaction are especially preferred.

In a preferred embodiment, the multisystem test means comprises a plurality of components associated with at least two reaction systems, respectively functional under different first and second reaction parameters, at least one of said components being responsive to the presence of said constituent in a first reaction system under said first reaction parameters, and at least one other of said components being effective after contact with the sample to produce said second reaction parameters under which a second reaction system is functional.

In another preferred embodiment, a multisystem test means is provided wherein at least one of said components functional to change said reaction parameters is encapsulated so as to be releasable by contact with the sample and effective after such release to produce said second reaction parameters under which a second reaction system is functional. Microcapsules are preferably used for encapsulation and can be formed by any conventional microencapsulation technique so as to contain a component effective to change the reaction parameters. The microcapsules are preferably osmosensitive, release of their contents being effected thereby. They can also be formed of material soluble in the sample solution. In addition to the component for changing reaction parameters, other components may also be encapsulated, such as those optimally reactive under reaction parameters of the second reaction system.

In another embodiment of the multisystem test means, the at least one component functional to change said reaction parameters comprises at least two components which are interreactive after contact with the sample to produce said second reaction parameters under which a second reaction system is functional. The interreactive components are, in a preferred embodiment, a catalyst, such as an enzyme, and its substrate. One or both of the interreactive components can optionally be encapsulated in microcapsules so as to embody more than one aspect of the invention.

In yet another embodiment of the invention, the multisystem test means comprises a plurality of components associated with at least two reaction systems, respectively functional under different reaction parameters, at least one of said components being responsive to the presence of said constituent in a second or later reaction system, and at least one other of said components effective in a first reaction system to inactivate a substance in the sample which interferes with said constituent responsive component. The constituent responsive component is preferably encapsulated, or otherwise sequestered for release after reaction of the interference-inactivating component. Protective determinant site binding and other well known techniques are applicable.

The multisystem test means is envisioned as a composition having the components defined in relation with the various embodiments identified above. The test means may also be incorporated with a carrier, such as a bibulous or non-bibulous matrix or other compositions such as binders, to form devices such as dip-and-read test devices or tablets, respectively.

In one embodiment, the device of the present invention can be prepared by incorporating, such as by simultaneous or sequential impregnation, a carrier matrix with at least one component responsive to the sample constituent in at least one reaction system and with the components effective for changing reaction parameters. When the carrier matrix is incorporated by impregnating with a liquid solution, the matrix so prepared is then subjected to drying. When microcapsules are used to encapsulate components, this encapsulation is normally done prior to and independent of their incorporation with the carrier matrix. Whether the microcapsules contain constituent responsive components or components effective for changing reaction parameters, they are preferably incorporated with the matrix after incorporation of the other components. The microcapsules may be impregnated throughout the carrier matrix, layered thereon, or consolidated in a centrally located portion. The device may be associated with a support member, such as an organo-plastic handle, if desired.

In another embodiment, the device can take the form of a tablet. Any conventional technique of tablet manufacture, such as pressing or molding processes, may be employed to incorporate the composition into a conveniently usable tablet. Binders, especially those which disintegrate or are soluble in the solvent of a liquid test sample, may be used to provide structural integrity before use.

The multisystem test means may be used free of matrices, tableting agents or other carriers, when intended for the testing of liquid samples, by contacting it with the sample. Response to the sample constituent to be determined is effected by formation of a chromophoric complex, oxidation-reduction reaction, antigen-antibody or enzyme-substrate complex formation, or other detectable change.

Preferably, the multisystem test means is used in the form of a solid preparation such as a device designed for convenience and reliability. The device is immersed in or otherwise contacted with a liquid sample to be tested. At least one of the components incorporated with or impregnated in the carrier matrix reacts with or is otherwise responsive to the presence of the constituent to be detected. At least one other of said components is responsive to contact with the sample under reaction parameters at which a first reaction system is functional to change said reaction parameters to those under which at least one other reaction system is functional. Response to the constituent to be detected can occur under reaction conditions or parameters existent at the time of contact between the device and the sample to be tested or in a later reaction system under previously altered reaction parameters.

Activation of the constituent effective to change reaction parameters can include, for example, release of encapsulated components or interaction of a catalyst, such as an enzyme, and its substrate. Thus, a catalyst and substrate may interact previous to, contemporaneously with, or subsequent to the response of the constituent responsive component. The enzyme and substrate interaction may even begin prior to constituent detection to provide a parameter change subsequent thereto provided they are in such relative proportions so as not to change reaction parameters until after a predetermined delay period.

The microcapsule embodiment provides for delayed release of the component for changing reaction conditions or for the constituent responsive component. After a predetermined delay period the solvent portion of the sample, being permeable to the capsule wall, enters the capsule as a result of the osmotic driving force. An osmotic gradient is produced sufficient to cause release of the capsule contents. The rate and extent of release of the capsule contents is a function of the initial osmotic gradient and characteristics of the capsule wall.

The sample is observed after the reaction systems provided for by the device have been allowed to go forward. In addition to visual comparison, various instrumental methods may also be employed to determine the change developed, thus increasing the accuracy of the test by obviating the subjective determination of color by the human eye.

DESCRIPTION OF THE PREFERRED EMBODIMENTS

Although specific terms are used in the following description for the sake of clarity, these terms are intended to refer only to the particular embodiments of the invention selected for exemplary illustration, and are not intended to define or limit the scope of the invention.

The term carrier matrix refers to bibulous and non-bibulous matrices which are insoluble in and maintain their structural integrity when exposed to physiological or other liquids. Suitable bibulous matrices which may be used include paper, cellulose, wood, synthetic resin fleeces, glass fiber, non-woven and woven fabrics and the like. Non-bibulous matrices include organo-plastic materials like polypropylene. For convenience the matrix can be associated with an insoluble support member such as polystyrene.

Alternatively, the inert carrier may be embodied in the form of a pressed or molded tablet containing conventional carrier material like disintegration agents, such as carboxymethylcellulose or starch; filling materials, such as lactose or phosphates; and lubricants, such as talc, stearic acid, or paraffin.

Microcapsules useful in the present invention can be prepared by a variety of well known methods such as those described in Greyson, U.S. Pat. No. 4,015,462; *Agnew. Chem. Internatl. Edit.* 14:539 (1975); and Adams, U.S. Pat. No. 3,092,463. Such methods include chemical encapsulation techniques like interfacial polycondensation or coacervation and physiomechanical techniques such as centrifugation or spray drying. Interfacial polycondensation, phase separation and polymerization techniques are preferred for ease of preparation of the microcapsules. The term osmosensitive refers to the ability of the capsule wall to react to internal hydrostatic pressure by changing in physical characteristics to allow the release of the internal phase.

The activity of the enzyme preparations used in the examples is measured by the number of units of activity per milligram of dry weight. The Commission on Enzymes of the International Union of Biochemistry has defined an International Unit (I.U.) of enzyme activity as 1 micromole ($\mu$mol) of substrate utilized per minute under specified conditions of pH and temperature control. This definition is intended unless otherwise indicated.

The examples shown are merely illustrative and are not to be construed as a limitation of the invention. One skilled in the art will be able to make such variations, substitutions and changes in the ingredients and parameters as may seem desirable.

EXAMPLES I AND II

In nitrite detection by a single phase test device, diazotization of an aromatic amine must take place at low pH, and the diazotized amine must then couple with another species at that same low pH. This limits greatly the coupling components which can be used to a relatively small number of aromatic amines and their derivatives.

However, if a test starts at acid pH and then becomes basic the number of coupling components which can be used becomes much larger, and includes for example a number of phenols and naphthols. This can be undertaken in a single testing operation only by using a device according to the present invention as is comparatively illustrated by the following preparations.

I. (a). An impregnating solution having a pH of about 2 was prepared in 75 milliliters (ml) of methanol by adding the following ingredients:
1. 0.13 grams (g) p-arsanilic acid (aromatic amine)
2. 3.0 g malonic acid
3. 25 ml of 2.0% solution of hydrolyzed Gantrez AN 139 [poly(maleic anhydride-methyl vinyl ether) GAF Corp., New York, New York, 10020]
4. 0.75 g sodium lauryl sulfate
5. 0.3 g 1-napthol-3,6-disulfonic acid disodium salt (coupling agent).

Sheets of Whatman No. 17 filter paper (Whatman Inc. Clifton, New Jersey, 07014) 10 centimeters (cm) × 10 were impregnated to saturation with the above impregnating solution, dried at 95° C. for 10 minutes, and cut into pieces 1 centimeter (cm) × 1 cm.

(b). Another single phase test device was prepared exactly as in (a) above, with the exception that the pH of the impregnating solution was adjusted to about 6 by addition of 15 ml of 2M citrate buffer to the solution and omission of the malonic acid.

(c). A multisystem test device according to the present invention was prepared as follows. Sheets of Whatman paper 10 cm × 10 cm in size were saturated with the impregnating solution of I(a) and dried as above. They were then coated with a monolayer of 70–80 mesh polyamide microcapsules, prepared by encapsulation of an aqueous solution containing 13.2 g/dl aqueous NaOH and desiccating to dryness.

Devices prepared according to (a), (b), and (c) above were tested by application of three drops of sample per 1 cm × 1 cm test device. The sample contained 10 milligrams/deciliter (mg/dl) $NaNO_2$ in distilled water and results were observed after 3 minutes. The test devices prepared in (a) and (b) failed to detect 10 mg/dl nitrite while device (c) readily indicated detection by turning bright orange.

A composition according to the present invention is formed when 0.13 g p-arsanilic acid, 3.0 g malonic acid, and 0.3 g 1-napthol-3,6-disulfonic acid disodium salt are combined directly with the polyamide capsules described in I(a). The proportion of encapsulated and non-encapsulated ingredients can be varied according to the rate and level of pH change desired and is preferably around 10.0 g of microcapsules.

The composition prepared above is tested by contacting it with three drops of the sample used above in 2 ml spot plate wells (Coors Porcelain Co., Golden, Colo. 80401). The test composition readily detects nitrite as indicated by the resultant color change.

II. In this experiment single phase test devices (a) and (b) were prepared exactly as in I (a) and I (b), respectively, above.

(c) A multiphasic test device according to the present invention was prepared as follows. A sheet of Whatman paper 10 cm × 10 cm in size was impregnated to saturation in a solution prepared as in I (a) above, with the exception that the 1-naphthol-3,6-disulfonic acid disodium salt was omitted, and then dried as previously described. These sheets were then coated with a monolayer of 70–80 mesh polyamide capsules which were prepared by encapsulating an aqueous solution containing 3.3% 1-naphthol-3,6-disulfonic acid disodium salt and 13.2 g/dl aqueous NaOH and desiccating to dryness. These sheets were cut to 1 cm × 1 cm squares to form devices.

Devices prepared according to II (a), (b), and (c) above were tested by application of three drops of sample per 1 cm × 1 cm square. The sample contained 10 mg/dl $NaNO_2$ in distilled water and results were observed after 3 minutes. The test devices prepared in (a) and (b) failed to detect 10 mg/dl nitrite while device (c) readily detected it as indicated by turning bright orange.

Thus, in both of these examples, if the pH is always low, then diazotization can take place, but no coupling.

If the pH is always high, then coupling can occur, but no diazotization. Only if the pH is first low for diazotization and then high for coupling will the device detect nitrite.

EXAMPLES III-V

In analyses for acid phosphatase, observed in pathological conditions such as metastatic carcinoma of the prostate, the hydrolytic action of the enzyme must be studied at pH 4.5, while some of the most convenient substrates are not observable except at basic pH. This limits greatly the number of substrates which can be detected in this way.

III. This is illustrated, in one test system, as follows:

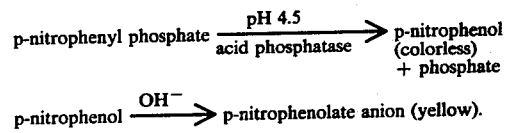

This can be undertaken in a single testing operation only by using a test device prepared according to the invention, as exemplified by comparative testing of the following three reagent test strip preparations:

(a) A single phase test device was prepared as follows. A sheet of Eaton-Dikeman 204 (E & D) filter paper (Eaton-Dikeman, Mount Holly Springs, Pennsylvania 17065) 10 cm × 10 cm was first impregnated to saturation in 25 ml of 0.02 Molar (M) sodium citrate buffer (pH 5.0) and dried at 60° C. It was then saturated in a 20 ml solution of methanol containing 0.3 g of p-nitrophenylphosphate sodium salt and dried at 60° C. The impregnated sheets were cut to 1 cm × 1 cm to form devices.

(b) In preparation of a multiphasic test device according to the invention, the same two first dips were carried out as in III (a) above. The sheet was then coated with a monolayer of polyamide microcapsules (70-80 mesh), prepared by encapsulation of an aqueous solution containing 13.2 g/dl aqueous NaOH and desiccating to dryness. The sheets were cut as above to form devices.

(c) In the third preparation, E & D paper was first impregnated to saturation in 0.1M Tris (hydroxymethyl) aminomethane (TRIS) buffer at pH 8.0 and then dried at 60° C. The second dip was the same as in III (a) above. The paper sheets so impregnated were cut as above to form devices.

The test devices so prepared were tested by administering 2 drops of a solution of 10 mg/ml (20 units*/mg) of wheat germ acid phosphatase (Research Products, Miles Laboratories, Inc., Elkhart, Indiana 46514) in 0.02M citrate buffer thereto and observed after 5 minutes. Strips (a) and (c) gave no color while strip (b) turned yellow. This shows that at pH 5 hydrolysis occurs, but the p-nitrophenol remains colorless (strip a). At pH 8.0, no hydrolysis occurs (strip c). Only when the pH is first low, to permit hydrolysis, and then high, to permit color formation, is the color produced to indicate detection of acid phosphatase.
*That amount of enzyme catalyzing the liberation of 1 μmol p-nitrophenol per hour at pH 4.8 and 37° C.

IV. Another system for detection of acid phosphatase occurs according to the following reaction scheme:

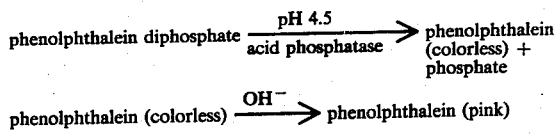

In this experiment single phase and multisystem test devices (a), (b) and (c) are prepared as in III (a), (b) and (c), respectively, above, except that the p-nitrophenyl phosphate is replaced by phenolphthalein diphosphate.

Devices prepared according to IV (a), IV (b) and IV (c) above are tested as in Example III. The test devices prepared in (a) and (c) fail to detect acid phosphatase while the multisystem test device readily indicates detection by turning pink.

V. Analysis for acid phosphatase can also be undertaken in a single testing operation by using a test device prepared according to another embodiment of the invention which does not make use of microencapsulation, as exemplified by comparative testing of the following three reagent test device preparations:

(a) A single phase test device is prepared as follows. A sheet of E & D filter paper 10.16 cm × 10.16 cm is first impregnated to saturation in 25 ml of 0.02 Molar (M) citrate buffer (pH 5.0) and dried at 60° C. It is then saturated with a 20 ml solution of methanol containing 0.3 g of p-nitrophenylphosphate sodium salt, dried at 60° C., and cut to 1 cm × 1 cm squares to form devices.

(b) In preparation of a multiphasic test device according to the invention, a sheet of E & D paper 10.16 cm × 10.16 cm is impregnated to saturation in 20 ml of 0.02M citrate buffer pH 5.0 containing urease (2000IU/ml)* and dried at 60° C. It is then saturated with 20 ml methanol containing 0.3 g p-nitrophenylphosphate sodium salt and 3.0 g urea, dried at 60° C., and cut as above to form devices.
*IU for urease is defined as the number of μmols of ammonia formed per minute.

(c) In the third preparation, E & D paper is first impregnated to saturation with 0.01M TRIS buffer at pH 8.0 and then dried at 60° C. The second dip is the same as in (a) above.

The test devices so prepared are tested as in Examples III and IV. Test devices (a) and (c) give no color while test device (b) turns yellow.

A composition is prepared when the urease containing citrate buffer solution and the urea solution are lyophilized and intermixed rather than being incorporated with a carrier. When tested by contacting with a test sample, resultant color change is to a yellow identical to that observed in the device preparation of this example (V).

Thus, in these examples, only when the pH is first low, to permit hydrolysis, and then high, to permit color formation, is color produced to indicate detection of acid phosphatase.

EXAMPLES VI AND VII

Devices used to analyze for β-glucuronidase are prepared, according to the invention, as described in the examples below.

VI. A multiphasic test device according to the present invention is prepared having the following reaction scheme:

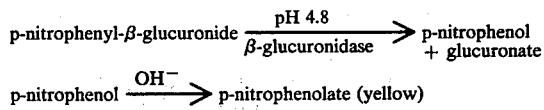

A sheet of Whatman paper 10 cm × 10 cm in size is impregnated to saturation in 20 ml of a solution of 60 mg p-nitrophenyl-β-glucuronide dissolved in 20 ml of water, and dried at 60° C. for 10 minutes. The sheets are then coated with a monolayer of polyamide microcapsules (70-80 mesh) prepared by encapsulation of an aqueous solution containing 13.2 g/dl aqueous NaOH and desiccating to dryness. The sheets so prepared are cut to 1 cm × 1 cm to form devices.

These devices so prepared are tested by immersion in 1 ml of 4 mg/dl β-glucuronidase (0.25 IU/mg)* in 0.01M acetate buffer pH 4.8 at 40° C. and are observed in 5 minutes while maintained on a heated block at 37° C. They readily detect the presence of β-glucuronidase as indicated by the appearance of a yellow color.

*IU for β-glucuronidase would be defined by reaction with phenolphthalein β-glucuronide.

VII. Another multiphasic test device according to the invention is parpared as in VI above, except that the paper is impregnated with 20 ml of a solution of 100 mg of phenophthalein-β-glucuronide in 20 ml of distilled water. This is illustrated by the following reaction scheme:

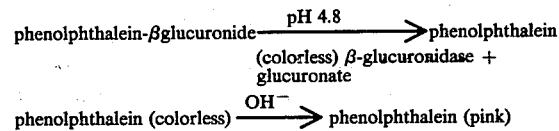

The devices so prepared, when tested as in Example VI, readily detect the presence of β-glucuronidase with the appearance of a pink color.

EXAMPLE VIII

Certain detection systems, such as those for hemoglobin in urine, are susceptible to the presence of interfering substances like ascorbate. Potent interference-removing agents, such as ascorbate oxidase, are however inactivated by the hemoglobin detection reagents.

Now, by use of the present invention, the ascorbate oxidase is permitted to remove the interfering ascorbate in a first reaction system while the hemoglobin detecting reagents are kept away from the ascorbate oxidase by encapsulation. The delayed release of the hemoglobin detecting reagents then occurs permitting the uninhibited detection of hemoglobin in a second reaction system. This is illustrated by the present example.

A 10 cm × 10 cm piece of E & D paper is dipped in 20 ml of 0.1M phosphate buffer pH 7 containing 2 mg ascorbate oxidase (500 IU/mg) and dried in an oven at 60° C. It is then coated with 20 ml of a suspension of microcapsules (37-200 μ) made from cellulose acetate butyrate (Product No. 381-20 Eastman Chemical Products, Inc. Kingsport, Tenn. 37622) which contain 0.35 g cumene hydroperoxide, 1.35 g triethanolamine borate, 0.08 g tolidine hydrochloride and 0.08 g 6-methoxyquinoline. The paper is then laminated to strips of polystyrene with double stick adhesive.

These strips, when dipped in urine containing 0.03 mg/dl hemoglobin and 50 mg/dl ascorbate turn blue, indicating the presence of hemoglobin in the urine, while strips containing the same ingredients but impregnated as above from a single homogeneous solution containing all the ingredients do not detect hemoglobin. Only when the ascorbate oxidase is able to catalyze the oxidation of ascorbate to dehydroascorbate prior to release of the ingredients for hemoglobin detection does the strip detect the hemoglobin. Otherwise the ascorbate oxidase is deactivated by the detection ingredients and the hemoglobin detection is made impossible by the presence of 50 mg/dl ascorbate.

Although the invention has been described with a certain degree of particularlity, it is understood that the present disclosure has been made only by way of example and that numerous changes in the details, combinations and arrangement of elements may be resorted to without departing from the scope of the invention.

What is claimed is:

1. A multisystem test composition effective for the determination of a sample constituent in a single operation comprising:
   at least one component reactive upon a single contact to chemically alter said sample constituent under reaction conditions incompatible with production of a detectable response, and
   at least one additional component effective upon said single contact with said sample to change reaction conditions after a time sufficient for reaction of said first component with said sample constituent from those incompatible with the production of a detectable response to those compatible with such a detectable response.

2. The multisystem test composition of claim 1 which comprises at least two components responsive to the presence of said constituent.

3. The multisystem test composition of claim 1 wherein the component reactive with the sample constituent is a chromogenic indicator.

4. The multisystem test composition of claim 1 wherein the component reactive with the sample constituent is a specific binding partner for the constituent to be detected.

5. The multisystem test composition of claim 1 wherein at least one component effective to change reaction conditions is effective to modify the pH.

6. The multisystem test composition of claim 1 wherein at least one component effective to change reaction conditions is effective to inactivate a substance which interferes with the component reactive with the sample constituent.

7. The multisystem test composition of claim 1 wherein at least one of said components is responsive to the presence of said constituent in a first reaction system under a first set of reaction conditions, and at least one other of said components is effective after contact with the sample to produce a second set of reaction conditions compatible with the production of a detectable response.

8. The multisystem test composition of claim 1 wherein at least one of said components effective to change reaction conditions is encapsulated in a capsule so as to be releasable by contact with the sample and effective after such release to produce conditions compatible with the production of a detectable response.

9. The multisystem test composition of claim 8 wherein said capsule is osmosensitive.

10. The multisystem test composition of claim 7 wherein the at least one component effective to change said reaction conditions comprises at least two components which are interreactive after contact with the sample to produce said second reaction conditions compatible with the production of a detectable response.

11. The multisystem test composition of claim 10 wherein the interreactive components are specific binding partners.

12. The multisystem test composition of claim 11 wherein the specific binding partners are an enzyme and its substrate.

13. The multisystem test composition of claim 1 wherein at least one of said constituent reactive components is responsive to the presence of a constituent in a second or later reaction system and at least one other of said components is effective in the first reaction system to inactivate a substance in the sample which interferes with the reaction of said sample constituent and said constituent reactive therewith.

14. The multisystem test composition of claim 13 wherein the constituent reactive component is encapsulated in a capsule for release after reaction of the interference-inactivating component.

15. A multisystem test device which comprises a carrier and, incorporated therewith, the composition of claim 1.

16. A multisystem test device which comprises a carrier and, incorporated therewith, the composition of claim 5.

17. A multisystem test device which comprises a carrier and, incorporated therewith, the composition of claim 6.

18. A multisystem test device which comprises a carrier and, incorporated therewith, the composition of claim 7.

19. A multisystem test device which comprises a carrier and, incorporated therewith, the composition of claim 8.

20. A multisystem test device which comprises a carrier and, incorporated therewith, the composition of claim 10.

21. A multisystem test device which comprises a carrier and, incorporated therewith, the composition of claim 11.

22. A multisystem test device which comprises a carrier and, incorporated therewith, the composition of claim 12.

23. A multisystem test device which comprises a carrier and, incorporated therewith, the composition of claim 13.

24. A multisystem test device which comprises a carrier and, incorporated therewith, the composition of claim 14.

25. A method for preparing a multisystem test device which method comprises incorporating a carrier with the composition of claim 1.

26. A method for determination of a constituent in a sample requiring reaction systems which are effective under different reaction conditions which method comprises contacting the sample with the composition of claim 1 and observing any detectable reaction.

27. A method for determination of a constituent in a sample requiring reaction systems which are effective under different reaction conditions which method comprises contacting the sample with the multisystem test device of claim 15.

28. A test composition for the determination of acid phosphatase comprising:
   a first component reactive with said acid phosphatase under acid conditions to form a colorless intermediate, said first component being selected from p-nitrophenyl phosphate and phenolphthalein diphosphate, and
   a second component comprising an enzyme and its substrate which interreact to change said acid conditions to alkaline conditions after a time sufficient for said intermediate to be formed whereby said colorless intermediate is ionized to a detectable color.

29. A test composition for the determination in a single operation of nitrite using components which are reactive only under incompatible reaction conditions comprising:
   an aromatic amine component reactive with said nitrite under acid conditions to form a diazotized amine,
   a coupling agent component reactive with the diazotized amine under alkaline conditions, and
   a component effective to change said reaction conditions from said acid conditions to said alkaline conditions after a time sufficient for said diazotized amine to be formed.

30. A test composition for the determination of β-glucuronidase using components requiring incompatible reaction conditions comprising:
   a first component reactive under acid conditions with said β-glucuronidase to form a colorless intermediate, said first component being selected from p-nitrophenyl-β-glucuronide and phenolphthalein glucuronide, and
   a component effective to change said reaction conditions from said acid conditions to alkaline conditions, after a time sufficient for said intermediate to be formed, whereby said colorless intermediate is ionized to produce a detectable color.

31. A test composition for the determination in a single operation of hemoglobin in a sample containing interfering substances using incompatible components effective under different reaction conditions, said composition comprising:
   a hemoglobin-responsive component susceptible to inactivation by the interfering substances,
   an interference-removing component susceptible to inactivation by the hemoglobin-responsive component, and
   wherein the hemoglobin-responsive component is sequestered from the interfering substances and the interference removing component for a time sufficient for the interference-removing component to remove the interfering substances.

32. The test composition of claim 31 wherein microcapsules are employed to sequester the hemoglobin-responsive component.

33. The test composition of claim 31 wherein the hemoglobin-responsive component comprises cumene hydroperoxide, triethanolamine borate, o-tolidine hydrochloride and 6-methoxyquinoline.

34. The test composition of claim 31 wherein the interference-removing component is ascorbate oxidase.

* * * * *